United States Patent [19]

Rawlings et al.

[11] Patent Number: 5,010,883
[45] Date of Patent: Apr. 30, 1991

[54] SURGICAL DRESSING

[75] Inventors: David A. Rawlings, Stansted Mountfitchet; William D. Potter, Bishops Stortford Hertfordshire, both of Great Britain

[73] Assignee: Smith & Nephew Associated Companies plc, United Kingdom

[21] Appl. No.: 349,393

[22] Filed: May 8, 1989

Related U.S. Application Data

[63] Continuation of Ser. No. 143,624, Jan. 12, 1988, abandoned, which is a continuation of Ser. No. 574, Dec. 31, 1986, abandoned, which is a continuation of Ser. No. 682,606, Dec. 17, 1984, abandoned.

[30] Foreign Application Priority Data

Dec. 24, 1983 [GB] United Kingdom ................ 8334484

[51] Int. Cl.$^5$ .................... A61F 13/00; A61L 15/00; B32B 3/26
[52] U.S. Cl. .................................. 128/155; 128/156; 428/220; 428/305.5
[58] Field of Search ................. 128/155, 156, 132 D; 428/220, 305.5

[56] References Cited

U.S. PATENT DOCUMENTS

| | | | |
|---|---|---|---|
| 1,956,695 | 5/1934 | Reinitz | 128/156 |
| 1,967,923 | 7/1934 | Connolly | 128/268 |
| 2,647,100 | 7/1953 | Salditt | 128/156 |
| 2,871,218 | 1/1959 | Schollenberger | 128/156 |
| 2,893,388 | 7/1959 | Ganz | 128/156 |
| 2,923,298 | 2/1960 | Dockstader et al. | 128/296 |
| 3,018,881 | 1/1962 | Wall | 206/56 |
| 3,055,368 | 9/1962 | Baxter | 128/283 |
| 3,121,021 | 2/1964 | Copeland | 117/122 |
| 3,285,245 | 11/1966 | Eldredge et al. | 128/156 |
| 3,483,018 | 12/1969 | Waldman | 117/68.5 |
| 3,520,306 | 7/1970 | Gardner | 128/335 |
| 3,520,949 | 7/1970 | Shepherd et al. | 260/857 |
| 3,521,631 | 7/1970 | Gardner | 128/156 |
| 3,526,224 | 9/1970 | Potts | 128/156 |
| 3,579,628 | 5/1971 | Gander et al. | 424/28 |
| 3,645,835 | 2/1972 | Hodgson | 161/146 |
| 3,658,065 | 4/1972 | Hirsch | 128/296 |
| 3,709,221 | 1/1973 | Riely | 128/156 |
| 3,821,136 | 6/1974 | Hudgin et al. | 260/9 |
| 3,822,238 | 7/1974 | Blair et al. | 260/75 NK |
| 3,870,041 | 3/1975 | Davies | 128/156 |
| 3,888,247 | 6/1975 | Stenvall | 128/155 |
| 3,927,669 | 12/1975 | Glatt | 128/156 |
| 3,975,350 | 8/1976 | Hudgin et al. | 260/30.4 |
| 4,061,618 | 12/1977 | Stanley et al. | 260/29.2 |
| 4,156,066 | 5/1979 | Gould | 528/73 |
| 4,156,067 | 5/1979 | Gould | 528/73 |
| 4,219,019 | 8/1980 | Coates | 128/156 |
| 4,231,357 | 11/1980 | Hessner | 128/156 |
| 4,308,623 | 1/1982 | Voorhees | 2/175 |
| 4,341,207 | 7/1982 | Steer et al. | 128/155 |
| 4,452,845 | 6/1984 | Lloyd et al. | 428/220 |

FOREIGN PATENT DOCUMENTS

| | | |
|---|---|---|
| 153276 | 9/1953 | Australia . |
| 682871 | 3/1964 | Canada . |
| 0006714 | 1/1980 | European Pat. Off. . |
| 0028452 | 5/1981 | European Pat. Off. . |
| 0050035 | 10/1981 | European Pat. Off. . |
| 0045592 | 2/1982 | European Pat. Off. . |
| 0050514 | 4/1982 | European Pat. Off. . |
| 0051935 | 5/1982 | European Pat. Off. . |
| 0059049 | 9/1982 | European Pat. Off. . |
| 0081988 | 6/1983 | European Pat. Off. . |
| 0091800 | 10/1983 | European Pat. Off. . |
| 0107915 | 5/1984 | European Pat. Off. . |
| 648733 | 1/1951 | United Kingdom . |
| 761840 | 11/1956 | United Kingdom . |

Primary Examiner—Kriellion Morgan
Attorney, Agent, or Firm—Jacobs & Jacobs

[57] ABSTRACT

An adhesive dressing for use on moist wounds which comprises a pressure sensitive adhesive-coated wound contacting first layer in which there are present holes capable of transmitting liquid water and a moisture vapor permeable, continuous film. The continuous film is attached to the first layer in such a way as to form a reservoir into which water can pass through the holes in the first layer and can evaporate from the reservoir through the continuous film. The adhesive coated first layer has a moisture vapor permeability of less than 300 gm$^{-2}$ 24 hr$^{-1}$ at 37° C. and 100% to 10% relative humidity difference and the continuous film has a moisture vapor permeability which is greater when in contact with liquid water than when not in contact with liquid water. Optionally, an intermediate water transmitting layer may be present between the first layer and the continuous film.

16 Claims, 2 Drawing Sheets

SURGICAL DRESSING

CROSS-REFERENCE

This is a continuation of Ser. No. 143,624 filed Jan. 12, 1988, now abandoned, which is a continuation of Ser. No. 000,574 filed Dec. 31, 1986, now abandoned which is a continuation of Ser. No. 682,606 filed Dec. 17, 1984, now abandoned.

The present invention relates to adhesive, moisture vapour permeable surgical dressings for use on human bodies, for example in contact with moist wounds. In particular, this invention relates to a dressing comprising a continuous moisture vapour permeable film attached to the non-wound contacting surface of a first layer, said layer adapted to transmit water by having holes therein. The first layer carries on its wound contacting surface an adhesive layer capable of adhering the dressing to the skin.

It is desirable to allow the wound to heal in its moist state, especially if covered with a layer of wound exudate as this state is believed to be capable of accelerating wound healing. The problems with moist wound healing when the wound is covered with a surgical dressing is that a "blister" of exudate can form under the dressing which is not only unsightly and uncomfortable but may also cause the dressing to leak, thereby defeating the aim of sterility. Such an excess of exudate therefore needs to be removed before a harmful blister forms. Normal methods of aspiration however, may also lead to wound infection. Finally, in order to preserve wound healing in a moist environment, it is desirable not to remove all the exudate as a "dry" wound and hence a slower healing wound would result. An attempt to overcome these disadvantages is described in European Patent Application No. 90564 in which the preferred dressings comprise an adhesive coated moisture vapour permeable, liquid water impervious first layer which contains perforations as a wound contacting layer and an imperforate, moisture vapour permeable, liquid water impermeable film attached to the first layer to form a sealed reservoir into which exudate from a wound may pass. The water in the exudate evaporates through the imperforate film thereby avoiding blister formation. Both films are required to have permeability in excess of $300 gm^{-2} 24hr^{-1}$ when measured at 40° C. and 80% relative humidity difference. We have found that as a result when no exudate is being released from the wound moisture can be lost from the skin and wound area at a rate that risks the wound drying out especially around the perforations and hence sticking to the dressing. Removal of the dressing when this occurs could cause damage to the newly formed tissue. Surprisingly it has been found that by using a combination of (i) a first layer which is formed from a low moisture vapour permeable sheet material but is adapted to transmit liquid water by the presence of holes and (ii) a continuous film of a moisture vapour permeable sheet material which has greater permeability when in contact with water than when not in contact with water, the disadvantages found in earlier dressings may be avoided or mitigated.

The dressings of the present invention therefore mitigate the disadvantages of blister formation and wound adherence by providing a surgical dressing suitable for use on moist wounds on human bodies which comprises a continuous film having a moisture vapour permeability which increases as the amount of water with which the film is in contact increases and decreases as the amount of water decreases and a wound contacting first layer which is adapted to transmit water by the presence of holes which layer when uninterrupted has a low moisture vapour permeability this layer being attached to the continuous film so as to form a sealed portion or reservoir into which the wound exudate may pass.

Accordingly the present invention provides an adhesive dressing for use on moist wounds which dressing comprises a pressure sensitive adhesive-coated first layer which has holes therethrough capable of transmitting liquid water and a moisture vapour permeable continuous film attached to the first layer thereby forming a reservoir into which water can pass and evaporate therefrom which dressing is characterised in that the adhesive coated first layer has an uninterrupted moisture vapour permeability of less than $300 gm^{-2} 24hr^{-1}$ and the moisture vapour permeable continuous film has a moisture vapour permeability which is greater when in contact with liquid water than when not in contact with liquid water.

It will be appreciated that by employing a low moisture vapour permeable adhesive coated first layer, the dressings of this invention are radically different from those in the art which all attempt to employ highly moisture vapour permeable components.

By low moisture vapour permeability is meant a moisture vapour vapour permeability of less than $300 gm^{-2} 24hr^{-1}$ when measured at 37° C. and 100% to 10% relative humidity difference. By an "uninterrupted moisture vapour permeability" is meant the moisture vapour permeability of the material in the absence of holes therethrough capable of transmitting liquid water, i.e. the moisture vapour permeability of the uninterrupted material.

The dressings according to the invention have the advantage of allowing water to evaporate rapidly from the wound area in the presence of an excess of exudate in the environs of the wound but, as the amount of exudate diminishes, so does the rate of evaporation. The use of a low moisture vapour permeable layer in contact with the wound means that when non-exuding or not rapidly exuding the amount of exudate around the wound is enough to keep it moist without causing blistering of the dressing and will not cause the wound to dry out which may result in adherence of the dressing to the wound.

The continuous film suitably has the following moisture vapour permeability (MVP) characteristics which are determinable by the Payne Cup Method (as described hereinafter): a moisture vapour permeability when in contact with water, that is when the Payne Cup is inverted, of not less than $8000 gm^{-2} 24hr^{-1}$ measured at 37° C. and 100% to 10% relative humidity difference, and is preferably greater than $10,000 gm^{-2} 24hr^{-1}$ and a moisture vapour permeability when not in contact with water which is suitably not more than $4800 gm^{-2} 24hr^{-1}$ measured at 37° C. and 100% to 10% relative humidity difference and is preferably less than $4000 gm^{-2} 24hr^{-1}$ and more preferably less than $3600 gm^{-2} 24hr^{-1}$.

When the continuous film is attached to the first layer to form the dressing, the moisture vapour permeability of the dressing, as measured for example by means of an evaporimeter placed above the surface of the continuous film, when in contact with water or wound exudate will reflect the high value of the continuous film as liquid will pass through the openings in the first layer into the sealed portion and will be lost by evaporation through the continuous film. However, when the wound no longer produces exudate and the continuous film is not in contact with water the evaporation of moisture vapour will reflect the lower permeability of the combination of first layer and continuous film. The use of a low moisture vapour permeable adhesive coated first layer means the wound will not dry out and the advantageous moist conditions required for wound healing are not lost.

Polymer materials which are suitable for use as continuous films by possessing the desired enhancement of "wet" moisture vapour permeability compared to "dry" moisture vapour permeability, are those containing chemical groups generally considered to be hydrophilic. Such groups include hydroxyl, ether, ester, carboxyl, amine, amide and carbonyl groups. Thus suitable materials include hydrophilic polyurethanes, cellulose derivatives, polyether-polyamides, polyamides, cross-linked polyvinyl alcohols and the like.

It has been found that polyether polyurethanes are particularly suitable for use in the formation of such films. Favoured polyether polyurethanes are essentially free of reactive substituents such as hydroxy or carboxy groups. Such polyurethanes for use in this invention include random polymers containing units derived from diolic compounds and di-isocyanates.

The ether units in such hydrophilic polyurethanes for use in this invention may be notionally derivable from ethylene diol and a propylene or butylene diol; that is they will contain $CH_2CH_2O-$ units and $-CH_2CH_2CH_2O-$, $-CH_2CH(CH_3)O-$ or $-CH_2CH_2CH_2CH_2O-$ units. Preferably, the ether units in the polyurethane will contain $-CH_2CH_2O-$ and $-CH_2CH(CH_3)O-$ or $(CH_2)_4O-$ or mixtures thereof of which poly $-CH_2CH(CH_3)O-$ blocks are preferred. Desirably, the mole ratio of poly(ethylene glycol) to poly [(prop or but)ylene glycol)]— derivable blocks present in the hydrophilic polyurethanes varies between 1:1 to 1:30; preferably from 1:2 to 1:10; and more preferably from 1:2.5 to 1:4. The molecular weights of these blocks is suitably from 600 to 6000 and favourably from 900 to 4000, for example 1000 to 2000.

Preferably, such hydrophilic polyurethanes for use in this invention will contain residues of aliphatic diols of up to 10 carbon atoms and more preferably up to 4 carbon atoms (of which ethane diol is preferred) as chain extenders wherein the mole ratio of diol to polyglycol used in the preparation of the polymer is from 3:1 to 1:4; preferably, 5:2 to 1:3; and more preferably from 2:1 to 1:2.

The hydrophilic polyurethane should contain sufficient di-isocyanate residues to produce the water contents set forth above when the film is hydrated.

The hydrophilic polyurethane for use in this invention may contain di-isocyanate residues which may be residues of aromatic or aliphatic di-isocyanates such as 4,4'-diphenylmethane di-isocyanate, toluene di-isocyanate, 1,6-hexamethylene di-isocyanate or the like. Favoured di-isocyanates for use in the hydrophylic polyurethane of this invention are 4,4'-dicyclohexylmethane di-isocyanate (which is preferred) and 4,4'-diphenylmethyl di-isocyanate.

Less preferably than using aliphatic diol chain extenders, the hydrophilic polyurethane may employ equivalent quantities of aliphatic diamine or aliphatic aminol chain extenders of which ethylene diamine is preferred.

Similarly somewhat less preferably than using aliphatic diol chain extenders, the hydrophilic polyurethane may employ an aromatic diamine such as phenylenediamine, benzidine or diaminodiphenylmethane.

Less preferably than using a mixture of poly(ethylene glycol) and poly [(prop or but)ylene glycol)] derived blocks, the hydrophilic polyurethane may employ poly(ethylene glycol) derived blocks alone together with a higher proportion of chain extender and di-isocyanate.

More preferably, the hydrophilic polyurethane used in a dressing of this invention is essentially a single type of polymer (a product of the poymerisation of the same materials) although blends may be employed to form the hydrophilic polyurethane if desired.

Further favoured materials are polyether-polyamide block copolymers whose preparation and properties have for example been described in British Patent No. 1473972, French Patents Nos. 1444437 and 2178205 and U.S. Pat. No. 3839243. A particularly apt polyether-polyamide block copolymer is known as Pebax 4011 RN 00 (available from ATO Chemical Products (UK) Ltd.). This polymer has a water content of 55% (approx) when hydrated and a 'wet-MVP' of $>14000$ $gm^{-2}24hr^{-1}$ and a 'dry-MVP' of 4600 $gm^2 24hr^1$ for a 70 micron thickness of film at 37° C. and a relative humidity of 100-10%.

A further suitable, though less preferred material is a plasticized regenerated cellulose film such as cellulose acetate. A suitable film is Rayophane 325P (available from British Sidac Ltd.). This film has a 'wet-MVP' of $>14000 gm^{-2}24hr^{-1}$ and a 'dry-MVP' of $4100 gm^{-2}24hr^{-1}$ for a 30 micron film when measured at 37° C. and 100-10% relative humidity.

A further suitable, though less preferred material is a polyvinyl alcohol which has been cross-linked, usually by means of heat, to form an insoluble but water absorbent film. A suitable polyvinyl alcohol is available as Polyviol W28/20 (Trade Mark, available from Wacker-Chemie GmbH). This polymer may be cast finto a film from aqueous solution, dried and cross-linked using heat for example by autoclaving. This film has a 'wet-MVP' of $>13,000 gm^{-2} 24hr^{-1}$ and a 'dry-MVP' of 4800 (approx) $gm^{-2}24hr^{-1}$ for a 37.5 micron film when measured at 37° C. and 100% to 10% relative humidity difference.

Most suitably the continuous film will be from 15 to 80μm thick, will more usually be from 20 to 60μm thick and will preferably be from 22 to 50μm thick, for example 25, 30, 35 or 40μm thick.

Suitably also the continuous film will be formed from a hydrophilic polymer which when hydrated contains up to 90% by weight of water, favourably contains 5 to 50% water, more favourably from 10 to 40% of water and preferably from 20 to 30% by weight of water, for example 25% by weight of water.

A preferred hydrophilic polymer is a hydrophilic polyurethane which when hydrated contains from 10 to 40% by weight of water.

Suitable hydrophilic polyurethanes are those which are described in European Patent Application No. 59035 which is incorporated herein by cross reference. A preferred hydrophilic polyurethane is therefore a linear polyether polyurethane which when hydrated contains from 20 to 30% by weight of water.

The dressing of which the continuous film forms part should conform readily to the body area to which it is applied and should also be elastic. Such dressings have the advantage of adhering securely to the body by following the body contours and allowing the body to move without dislodging the dressing. Synthetic polymers are more conformable and elastic than natural polymers which tend to be stiff, inelastic and generally nonconformable. Synthetic polymers are therefore preferred for the continuous film.

It is further preferred that the continuous film should be transparent so that the wound may be observed. The continuous film is self supporting, that it is coherent when wet or dry and can be used without recourse to additional support such as fabric, net or the like.

In the dressings of the present invention the adhesive coated first layer when not possessing holes will have a low moisture vapour permeability, that is a moisture vapour permeability of less than $300 \text{gm}^{-2} 24\text{hr}^{-1}$. Such dressings have been found to provide better conditions for healing of wounds and may be retained in place for extended periods in use which reduces the risk of infection or retraumatisation of the wound whilst it is healing. Clearly this low moisture vapour permeability for the adhesive coated first layer may be achieved by either coating a first layer of high moisture vapour permeability with a continuous layer of adhesive of low moisture vapour permeability or by coating a first layer of low moisture vapour permeability with an adhesive which may be in the form of a continuous, microporous or pattern spread coating which may have a high or low moisture vapour permeability. The relationship between the moist vapour permeabilities of an adhesive coated layer and its component layers being described hereinafter. Thus the skilled man would appreciate which adhesives and which polyme films could be combined to provide a first layer of the correct moisture vapour permeability.

Material suitable for use as the first layer for use in dressings of this invention include elastic or non-elastic, conformable, natural or synthetic polymers. The sheet material of the first layer is adapted to allow transmission of water through the film, that is a water transmitting film by being perforated by means of holes. When used herein holes mean any shaped hole which is usually visible to the naked eye which passes through the film and its adhesive coat. Such holes include slits.

Materials which are suitable for forming the first layer and which are permeable to moisture vapour include those which are described in our copending European Patent Application No. 107915 at page 15 lines 5 to 23 and page 16 lines 6 to 16. A favoured first layer is polyurethane. The adhesive for use with such materials will give a low moisture vapour permeability to the adhesive coated material. Such adhesives suitable for use on skin are known in the art and include for example natural or synthetic rubber based adhesives.

It is presently preferred to use for the first layer materials which themselves have a low uninterrupted moisture vapour permeability.

Accordingly the present invention provides a moisture vapour permeable, adhesive surgical dressing comprising a conformable, liquid water impermeable, wound contacting first layer which is adapted to transmit liquid water by means of holes and which first layer has on its wound contacting surface a pressure sensitive adhesive layer suitable for adhering the dressing to the skin and a continuous, conformable, moisture vapour permeable film attached to the first layer forming a reservoir into which wound exudate passes and can evaporate therefrom is characterised in that the first layer has a low moisture vapour permeability and the continuous film has a moisture vapour permeability which is greater when in contact with water than when not in contact with water.

Materials which are suitable for forming the first layer and which have low moisture vapour permeability include polyolefin films, such as polyethylene, polybutadiene, polyolefin copolymers such as ethylene-vinyl acetate copolymers, polyisobutylene e.g. Oppanol (Trade Mark of BASF), styrene butadiene styrene block polymers e.g. Kratons (Trade Mark of Shell Chemicals Ltd.), polyesters and the like. A first preferred film is a polybutadiene. A more preferred film is made from a styrene-butadiene-styrene triblock copolymer.

Suitably the first layer will have a thickness of up to 150μm, more suitably will be from 15 to 100μm thick, most suitably will be 20 to 75μm thick and preferably 25 to 40μm thick, for example 25μm, 30μm, 35μm or 40μm.

Suitably a continuous sheet of the material which is adapted to form the first layer will have a moisture vapour permeability of less than $300 \text{gm}^{-2} 24\text{hr}^{-1}$ and more suitably between 20 and $280 \text{gm}^{-2} 24\text{hr}^{-1}$ and most suitably less than $100 \text{gm}^{-2} 24\text{hr}^{-1}$ when measured at 37° C. and 100% to 10% relative humidity. For example some preferred films described hereinafter will have a moisture vapour permeability of between 25 and $90 \text{gm}^{-2} 24\text{hr}^{-1}$ and preferably between 40 and $80 \text{gm}^{-2} 24\text{hr}^{-1}$ A second group of preferred films such as the styrene-butadiene copolymers will have an uninterrupted moisture vapour permeability of 200 to $260 \text{gm}^{-2} 24\text{hr}^{-1}$.

Suitably the first layer will be interrupted by means of perforations, for example circular holes. Such perforations will be capable of allowing the passage of liquid water and normally will be visible to the naked eye and may measure 0.1 to 2.5mm, for example 1.5mm in diameter. Usually the holes will be spaced 0.5 to 2.5cm from each other and may be arranged in parallel rows or in staggered rows.

Alternatively and preferably the first layer will be interrupted by means of slits. The slits may be from 0.3 to 1.5cm in length and more suitably 0.35 to 1.0cm in length for example 0.4cm, 0.5cm and 0.6cm and be spaced from 0.2 to 2.5cm from each other and preferably 0.3 to 1.5cm from each other. The slits may be straight, arcuate or in the form of two slits at right angles. It is preferred that the slits are arranged all in straight lines in parallel rows, for example 1cm apart and with 0.2cm between adjacent slits in any one row, in which case the slits are suitably 0.4cm long.

The continuous film is attached to the non-wound contacting side of the first layer so as to form a sealed portion or reservoir which is capable of holding wound exudate when in use. The attachment means includes heat sealing, ultrasonic welding, radio frequency welding or by means of an adhesive or adhesive tape depending on the nature of the polymers involved. It is preferred that the films are heat sealed together. The seal may be in the form of a border around the periphery of the reservoir portion but may also include seal lines within the border, for example to produce a quilted effect.

In one embodiment therefore, the continuous film and first layer will be coextensive and sealed together at least around their edges. In a second embodiment the first layer will extend beyond the periphery of the continuous film. Most aptly the first layer will extend beyond the periphery on two opposite edges. The seal may therefore be formed around the edge of the continuous film so leaving a margin of the first layer which contains holes or may be arranged to be unperforated. In a third embodiment, though less preferred, the continuous film may extend beyond the periphery of the first layer in which case the first layer mey be sealed around its periphery to the continuous film.

The dressings of the invention in which the continuous film and first layer are coextensive will aptly have dimensions of from 8cm×8cm to 40cm×40cm for example 8cm×8cm, 8cm×12cm, 10cm×10cm, 20cm×15cm, 20cm×30cm, 40cm×30cm and 40cm×40cm. It is clear that the size of dressing will be chosen depending upon the size of the wound upon which it is to be used for example the sizes 8cm×8cm and 8cm×12cm will be used on small wounds while the larger sizes are suitable for donor sites.

In those dressings of the invention in which there is a margin of either the continuous film or the first layer extending beyond the sealed portion this margin will be from 1 to 6 cm wide and preferably will be from 2 to 4cm wide. Smaller margins are usually found on smaller dressings, for example 2cm while the larger margin is found on the large dressings for example 4cm. This margin may be present in all four edges of the dressing but preferably is present only on two opposite sides.

The adhesive employed in the dressings of this invention must be compatible with the wound, that is it must not adhere to it. Suitable adhesives include synthetic polymers or mixtures thereof. Such adhesives may be selected from those described in British Patent Specification No. 1,280,631 and European Patent Application No. 35399. Suitable adhesives are formed from acrylate ester copolymers or polyvinyl ethyl ethers. If desired such adhesives may incorporate an antibacterial agent.

A preferred pressure sensitive adhesive comprises a blend of high and low viscosity polyvinyl ethyl ethers in particular adhesive composition A disclosed in British Patent Specification No. 1280631. Other preferred pressure sensitive adhesives comprise copolymers of acrylate ester with acrylic acid for example as disclosed in European Patent Application No. 35399 and in particular a copolymer of 47 parts by weight of butyl acrylate, 47 parts by weight of 2-ethylhexyl acrylate and 6 parts by weight of acrylic acid with an intrinsic viscosity of at least 1.9dl/g polymerised in acetone according to the general method given in the above European Application.

Suitably the adhesive is employed at a mass weight per unit area of 20 to $80gm^{-2}$, more suitably at 20 to $45gm^{-2}$ and preferably at 25 to $35gm^{-2}$, for example $29gm^{-2}$ or $32gm^{-2}$.

Suitably the adhesive layer is applied to the film of the first layer as a continuous layer prior to making the holes in the film, so that normally the adhesive layer will be interrupted during interruption of the film. Such adhesives which are applied continuously will have a moisture vapour permeability which is greater than $300gm^{-2}24hr^{-1}$ and more preferably greater than $500gm^{-2}24hr^{-1}$ when measured at 37° C. and 100% to 10% relative humidity.

Alternatively the adhesive layer may be in the form of a pattern spread or discontinuous spread adhesive layer using a conventional surgical adhesive prepared and spread by the method described in for example British Patent No. 819635. The adhesive may also be in the form of a porous or microporous layer.

Similarly if the continuous film forming the moisture vapour permeable layer extends beyond the periphery of the first layer, this may carry an adhesive on the exposed margin, that is on the body contacting surface. The adhesive may be continuous or pattern spread or porous and formed from the polymers as hereinbefore described as being suitable for adhesion to the skin.

In a further aspect of the present invention an intermediate layer is provided between the non-wound contacting surface of the first layer and the continuous layer. The intermediate layer will be water transmitting so as not to prevent the passage of water from the wound to the continuous film. The presence of the intermediate layer may in certain cases aid the manufacture of the dressing by preventing unwanted adherency of the continuous film to the first layer during, for example, the sterilisation process. The presence of the intermediate layer has further advantages in that it improves the handleability of the dressing and further slows down the rate of the evaporation of the moisture vapour from the surface of the continuous film which reduces the risk that the wound might dry out and stick to the dressing particularly around the holes in the first layer. The intermediate layer also appears to encourage flow of exudate through the holes by means of a wicking action and removes any risk of the first layer and continuous film adhering to each other in use which may prevent operation of the dressing. The intermediate layer may also carry a medicament which is released to the wound area in use. Suitably the medicament will be an antimicrobial agent, for example chlorhexidine or its salts or povidone iodine.

Materials suitable for forming the intermediate layer include woven and non-woven fabrics, nets, perforated films, hydrogels or hydrophilic polymers and the like which are water permeable. Aptly the intermediate layer is a non-woven fabric or a perforated film or an integral net. Preferably the layer is a non-woven fabric. Generally suitable non-woven fabrics will be formed from hydrophobic polymers such as polyolefins. Preferred non-woven fabrics include a spun bonded polypropylene fabric known as Novelin (Trade Mark, available from J. W. Suominen). In the manufacture of the dressings a piece of the non-woven fabric may be placed over the perforated area of the first layer, the continuous film placed on top of the non-woven fabric and all three layers sealed together around their edges or the continuous film may be simply only sealed to the first layer, thereby trapping the intermediate layer between the two.

Films, which when perforated, are suitable for use as an intermediate layer include polyolefin films and polyester films such as Melinex (Trade Mark, available from I.C.I. plc). Aptly these intermediate layers are perforated in a similar manner to the first layer as described hereinbefore, that is they are perforated with holes or slits. Surprisingly it has been found that it is advantageous to maintaining the moistness of the wound and to the progress of wound healing if the holes or slits in the first layer are not in register with the holes or slits in the intermediate layer.

Aptly when an intermediate layer is present, this layer is also transparent so that the progress of wound healing may be observed. However, in the case where the layer is a non-woven fabric the fabric may not be transparent, so the centre of this layer may be removed prior to sealing between the continuous film and the first layer so that the wound may still be observed.

When the intermediate layer of water transmitting material is in the form of a polymeric film then it will have a thickness similar to that used for the interrupted film that is up to 150 microns. If the intermediate layer is a non-woven or woven fabric then the layer tends to be thicker.

Thus in a further aspect the present invention provides an adhesive dressing suitable for use on moist wounds which dressing comprises a pressure sensitive adhesive-coated first layer which has holes therethrogh capable of transmitting liquid water and a moisture vapour permeable continuous film attached to the first layer thereby forming a reservoir into which water can pass and evaporate therefrom which dressing is characterised in that the adhesive coated first layer has a moisture vapour permeability of less than $300 \text{gm}^{-2} 24\text{hr}^{-1}$ and the moisture vapour permeable continuous film has a moisture vapour permeability which is greater when in contact with liquid water than when not in contact with liquid water and that there is a further water transmitting intermediate layer present between the first layer and the continuous film.

The materials which may comprise the continuous film and first layer are as hereinbefore described.

Optionally the first layer may also incorporate or may have attached to its surface remote from the continuous film a water-absorbing material such as a hydrogel such as Spenco (Trade Mark) or a hydrophilic foam such as Hypol (Trade Mark) foam. The presence of such a material does not interfere with the escape of excess water but provides a reservoir of exudate which remains.

When first put over the wound, the dressing is dry so the holes are relatively insignificant as the major area of the wound is covered by the first layer and the holes are themselves covered by the continuous (e.g. hydrophilic polyurethane) film. As the amount of wound exudate increases, tending to blister-formation, the exudate seeps through the holes, hydrating the hydrophilic polyurethane, the MVP of which increases so the water evaporates. Once the "blister" has subsided, the MVP of the continuous film decreases, but the wound still remains moist because most of its area is covered by the less permeable first layer.

Therefore in a further aspect the present invention provides a method of dressing an exuding wound on an animal body comprising placing over the wound a dressing of the present invention and adhering the dressing to the body and allowing the wound exudate to pass through the holes of the first layer into a reservoir and allowing moisture vapour from said exudate to escape by transmission through the continuous film.

In a preferred aspect the present invention provides a method of dressing a donor site on an animal body which comprises placing over the donor site a dressing of the present invention and adhering the dressing to the body and leaving in position for a period of from 3 to 20 days.

Dressings of the present invention are suitable for use on wounds including donor sites (split thickness), partial thickness burns, pressure sores and leg ulcers, which wounds exude large quantities of liquid and heal by reepithelialisation. These wounds will normally be dressed for a period of from 3 to 20 days and preferably for 7 to 14 days, when reepithelialisation of the wound could be complete.

Thus in a particularly preferred aspect the present invention provides a method of dressing a donor site on an animal body which comprises placing over the donor site a dressing of the present invention and adhering the dressing to the body and leaving in position for a period of from 7 to 14 days.

In a preferred method the dressing will have an intermediate layer between the adhesive coated first layer and the continuous film.

The dressings used in the method of dressing a exuding wound may be any of those hereinbefore described.

The method of dressing a wound using a dressing of the present invention may be applied to all exuding wounds such as burns, skin graft donor sites,.pressure sores, ulcers, surgical wounds and the like. It is an advantage of the dressing of the present invention that they may be left in place on the wound for extended periods of time with reduced risk of leaking, causing blister formation or adhering to the wound. The time over which a dressing may be left in place will vary depending on the type of wound and the form of any other treatment which may be given to the wound. A dressing may be left covering a skin graft donor site for up to 14 days without detrimental effect and can yield a healed wound at the end of that time.

Preferably, the dressing according to this invention is provided in sterilised form and, when self-adhesive, is adhered to a removable sterile backing sheet. Suitable removable backing sheets or release liners are those which are conventionally used in the art, that is release liners which are made of, or coated with polyethylene, polypropylene and fluorocarbons and silicone-coated release papers or polyester films. A preferred release liner is formed from silicone-coated release paper. Prior to use, the release liner is stripped from the adhesive coating of the dressing so that the dressing may then be applied to the skin. The dressing may be packaged in a bacteria-proof package such as a paper, plastic or aluminium foil pouch and sterilisation may be achieved in conventional manner, e.g. by use of gamma irradiation, heat or ethylene oxide.

Suitable forms of dressing and removable backing sheet(s) include ones similar to those described in European Patent Specification No. 51-935. Suitable hydrophilic polyurethanes for use include those described in European Patent Specification No. 50035.

In a preferred form of a dressing of the present invention the adhesive coated first layer extends beyond the edges of the continuous film on two opposite sides. The extended margins of the first layer may then be adhered to a non-adhesive polymer film, such as a polyester film, to form non-adhesive handles to aid the manipulation of the dressing when positioning on the body.

The polymer which is to form the non-adhesive layer or backing layer of the first layer may be extruded or cast (from a solution) onto a silicone release paper to give a film of the required thickness and weight when the solvent is removed. An adhesive film may be similarly cast on to a release paper. The backing layer may be transferred to the adhesive film by conventional transfer coating means. Alternatively the first layer may be cast onto one surface of a double sided release paper and the adhesive layer cast onto the first layer. The combined layers are then transferred to the other surface of the release paper so that the adhesive layer is covered by the release paper. The handles may be advantageously inserted during this transfer process. The combined films may then be formed into the first layer by punching holes of the appropriate diameter through the backing and adhesive layers and release paper. Alternatively slits of the appropriate length and shape may be cut through the backing layer and adhesive layer and release paper using a sharp blade or an array of such blades which give the correct pattern.

The continuous film may be cast from a solution of the appropriate hydrophilic polymer at the required thickness and weight. This film may be heat sealed or adhered around its edges to the non-adhesive side of the first layer. In other instances the continuous film may be formed by extrusion of the appropriate polymer to give a film of the required thickness. The continuous film may be sealed using a heated box-section so that the holes of the first layer fall within the sealed square so formed. Other dressings according to this invention may be prepared by methods known to those skilled in the a t.

The dressings may be formed to any appropriate size using the general preparative method described above for example dressings of smaller size 8cm×12cm may be used on small wounds while larger sizes, 30cm×30cm for 40cm×30cm may be used on large wounds or donor sites.

Preferred embodiments of the dressings of the present invention will be described with reference to the accompanying drawings which are by way of example only and in which.

Figure 1:
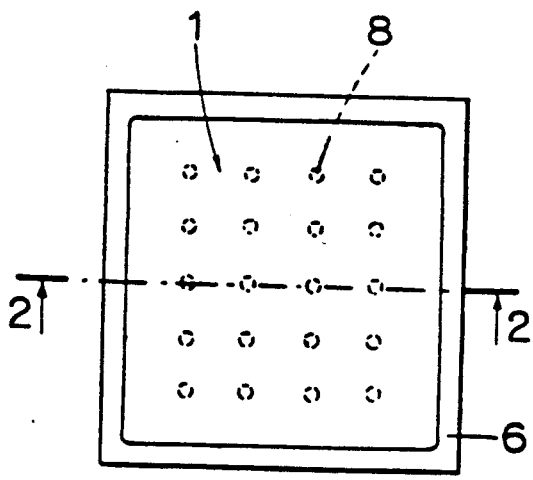
FIG. 1 shows a dressing from the wound contacting side in which the continuous film and first layer are coextensive.
Figure 2:
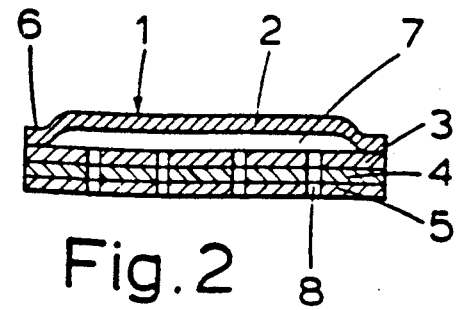
FIG. 2 shows a cross-section of the dressing of FIG. 1 along the line A—A.

FIGS. 1 and 2 show a dressing (1) comprising a continuous film (2), first layer (3), with an adhesive layer (4) on the wound contacting side and a release paper (5) which is removed from the adhesive layer (4) prior t use. The continuous film (2) is attached to the non-wound contacting side of the first layer (3) by means of a heat seal (6) which extends around the periphery of the dressing. The result of this seal line (6) is that a reservoir portion (7) is formed between the first layer (3) and the continuous film (2) into which wound exudate may flow via the perforations (8) which are shown (n this illustration as circular holes. The perforations (8) extend through the three layers (3), (4) and (5), for ease of manufacture. The dressings are packaged in a bacteria proof pouch prior to sterilisation so that the presence of perforations through the three layers is not detrimental to overall sterility prior to use. The heat seal (6) preferably is arranged to avoid crossing over any perforations and hence avoids the risk of bacteria entering the reservoir portion. The adhesive layer (4) is also continuous under the seal thereby preventing access to bacteria.

Figure 3:
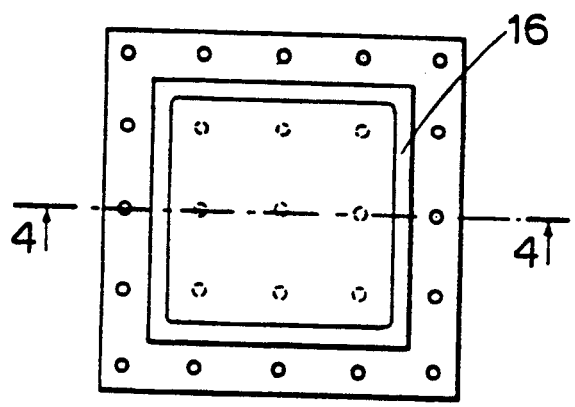
FIG. 3 shows a dressing from the wound contacting side in which the first layer extends beyond the periphery of the continuous film.
Figure 4:
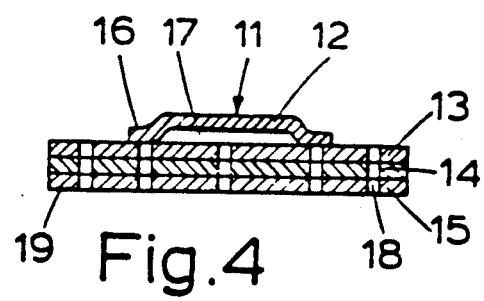
FIG. 4 shows a cross-section of the dressing of FIG. 3 along the line B—B.

FIG. 3 and 4 show a dressing (11) comprising a continuous film (12), first layer (13) with an adhesive layer (14) on the wound contacting side and a release paper (15). The continuous film (12) is attached to the first layer (13) by means of a heat seal (16). The first layer (13) extends beyond the periphery of the continuous film (12) to form an adhesive coated margin (19). The first layer (13) in this margin is perforated by means of circular holes (18) which help it prevent the underlying skin becoming macerated when the dressing is in place. The reservoir (17) is formed in a similar manner to that of earlier described dressings.

Figure 5:
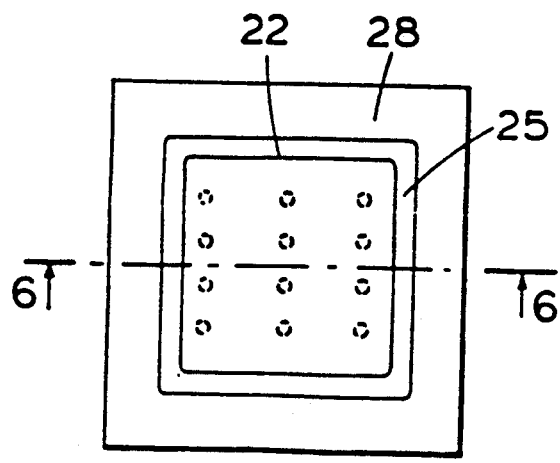
FIG. 5 shows a dressing from the wound contacting side in which the continuous film extends beyond the periphery of the first layer.
Figure 6:
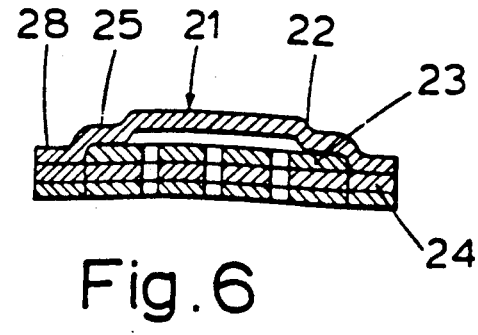
FIG. 6 shows a cross-section of the dressing of FIG. 5 along the line C—C.

FIGS. 5 and 6 show a dressing (21) comprising a continuous film (22) which extends beyond the periphery of the first layer (23). The adhesive layer (24) is present on both the first layer (23) and on the margin area (28) of the continuous film (22). Since the continuous film has a high moisture vapour permeability, the margin areas (28) will comprise a continuous film and continuous adhesive layer. The continuous film is heat sealed (25) to the first layer as previously.

Figure 7:
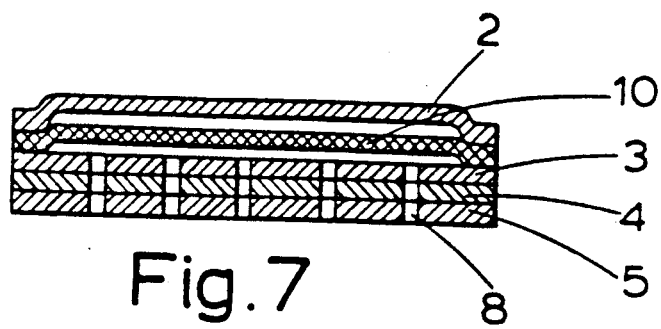
FIG. 7 shows a cross section of a dressing of the same type as that of FIG. 1 in which a film of non-woven fabric is present between the continuous film and first layer.

FIG. 7 shows a dressing of the same type as that of FIG. 1 except that a water transmitting non-woven fabric (10) is present between the continuous film (2) and the first layer (3).

In this embodiment the non-woven fabric is sealed into the dressing. The non-woven fabric effectively divides the reservoir (7) into two parts but does not prevent the free flow of exudate from the wound.

Figure 8:
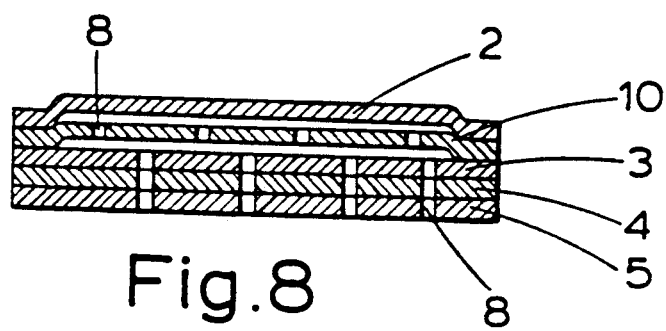
FIG. 8 shows a cross-section of a dressing of the same type as that of FIG. 1 in which a second water transmitting film is present between the continuous film and a first layer.

FIG. 8 shows a dressing similar to that shown in FIG. 7 except that the intermediate water transmitting layer (10) is a perforated film. The perforations in the film are circular holes and are arranged so as to be out of alignment with those (7) of the first layer.

Figure 9:
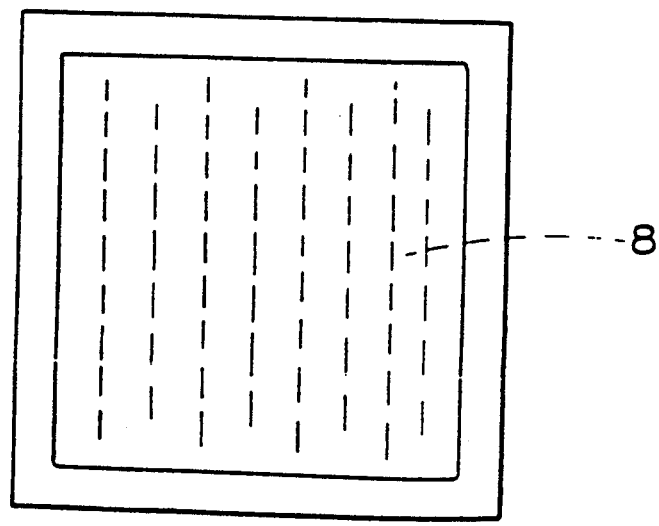
FIG. 9 shows a similar dressing to FIG. 1 except that slits are present instead of holes.

FIG. 9 shows a dressing similar to that shown in FIG. 1 except that the first layer (3) is interrupted by slits (7) instead of circular holes. When the dressing is applied under slight tension the slits tend to open slightly to aid the flow of wound exudate into the reservoir.

The following Examples are provided by way of illustration of this invention. The hydrophilic polyurethanes may be prepared as described in European Patent No 50035.

Example 1

Preparation of Adhesive Surgical Dressing

A film of syndiotactic 1,2-polybutadiene (JSR RB830 available from Japanese Synthetic Rubber Company) was formed by extrusion. The film had a thickness of 150μm. A piece of this film was taken and its moisture vapour permeability measured using the Payne Cup Method. The film was found to have a moisture vapour permeability of $79 gm^{-2} 24 hr^{-1}$ at 37° C. when measured at a relative humidity difference of 100% to 10%.

An acrylic ester copolymer formed by copolymerisation of 47 parts n-butyl acrylate, 47 parts 2-ethylhexyl acrylate and 6 parts acrylic acid in acetone solution was cast from acetone solution at 35% solids, onto a siliconised release paper. The solvent was removed to give a layer of polymer at a weight of 30gsm which had adhesive properties.

The adhesive layer was transfer coated onto the polybutadiene film to form a laminate. A piece of this laminate was taken and after removal of the release paper its moisture vapour permeability measured using the Payne Cup Method. The laminate was found to have a moisture vapour permeability of $52 gm^{-2} 24 hr^{-1}$ at 37° C. when measured at a relative humidity difference of 100% to 10%. A further piece of laminate on its release paper, 8cm×12cm, was taken and perforated with holes approximately 1cm apart, such a size of dressing would contain approximately 54 holes.

A 15% solution of a hydrophilic polyurethane, having a potential water content of 25% when hydrated, in industrial methylated spirits was mixed with 5% fine silica (Gasil 23, Crossfield Chemical Ltd.) and was cast onto silicone release paper to give a film of weight 40gsm. A piece of this film was taken and its moisture vapour permeability measured using the Payne Cup Method. The film was found to have a moisture vapour permeability of $2200 gm^{-2} 24 hr^{-1}$ when not in contact with water and of more than $13,000 gm^{-2} 24 hr^{-1}$ when in contact with water (when measured at 37° C. and 100% to 10% relative humidity difference). A piece of the film was cut to the same size as the laminate on its release paper, namely 8cm×12cm.

A piece of spun-bonded polypropylene, 8cm×12cm, was placed on the non-adhesive side of the polyisobutadiene film and the hydrophilic polyurethane film placed on top of this. The films were then sealed together around their edges using an impulse heat sealer to give the surgical dressing of the present invention.

In use the release paper is removed from the adhesive coated face of the perforated polybutadiene film and the dressing adhered around the wound. The wound exudate is free to pass through the perforations. Water vapour will subsequently evaporate from the surface of the continuous film thereby avoiding forming a blister of wound exudate beneath the dressing.

The dressing may be sealed into a bacteria proof pack and sterilised by conventional means prior to use.

Example 2

Preparation of Adhesive Surgical Dressing

A similar dressing to that described in Example 1 was prepared except that instead of perforating the adhesive-coated polybutadiene film with holes, the perforations took the form of slits approximately 5mm long, spaced 1.4cm apart.

Example 3

Preparation of Adhesive Surgical Dressing

A dressing similar to that described in Example 1 was prepared except that in place of a film of polybutadiene a film of polyethylene 22μm in thickness was used. The polyethylene film had a moisture vapour permeability of $78 gm^{-2} 24 hr^{-1}$ when measured using the Payne Cup Method at 37° C. and a moisture vapour permeability of $32 gm^{-1} 24 hr^{-1}$ when coated with adhesive. when coated with adhesive.

Example 4

Preparation of Adhesive Surgical Dressing

A dressing similar to that described in Example 1 was prepared except that in place of a film of polybutadiene a film of a styrene-butadiene-styrene triblock copolymer (Kraton 1101) 30μm in thickness was used. The Kraton 1101 film had a moisture vapour permeability of $260 gm^{-2} 24 hr^{-1}$ when measured using the Payne Cup Method at 37° C. and 100% to 10% relative humidity difference.

Example 5

Preparation of Adhesive Surgical Dressing

A dressing similar to that described in Example 1 was prepared except that in place of a film of polybutadiene a film of polyisobutylene 60μm in thickness was used.

Example 6

Preparation of Adhesive Surgical Dressing

A dressing using the same materials as those described in Example 1 was prepared except that the dimensions chosen for the laminate of release paper, adhesive layer and polybutadiene was 12cm×12cm. The laminate was perforated over its entire surface as before. The dimensions of the spun bonded polypropylene and hydrophilic polyurethane film were however restricted to 8cm×8cm. The films and laminate were sealed together using an impulse heat sealer around the edges of the polypropylene non-woven and polyurethane. Care was taken to avoid sealing over a perforation as this might result in an incomplete seal around the polyurethane film which would allow exudate to flow out of the dressing and consequently could allow bacteria in. The resultant dressing therefore had a sealed central portion 8cm×8cm and a 2cm margin of adhesive coated perforated film.

Example 7

Preparation of Adhesive Surgical Dressing

An acrylic ester copolymer formed by the copolymerisation of 47 parts n-butyl acrylate, 47 parts 2-ethylhexyl acrylate and 6 parts acrylic acid in acetone solution, was cast from acetone solution at 35% solids onto a siliconised release paper. The solvent was removed to give a layer of adhesive at a weight per unit area of 30gsm.

The adhesive layer was transfer coated onto a styrene-butadiene-styrene triblock copolymer film (Kraton 1101 film) 60μm in thickness by passage between a pair of rollers. This laminate on its release paper was perforated with knives to provide slits which were 4mm long, arranged in rows in which the distance between each row was 1cm and the distance between two slits in any one row was 0.2cm. The perforated laminate was cut into pieces 8cm×12cm. A portion of the adhesive-coated Kraton film was taken prior to perforation and its moisture vapour permeability measured by the Payne Cup method, was $237 cm^{-2} 24 hr^{-1}$.

A 15% w/w solution of a hydrophilic polyurethane, having a potential water content of 25% when hydrated, in industrial methylated spirits was mixed with 5% fine silica (Gasil 23, Crossfield Chemical Ltd.) and was cast onto silicone release paper to give a film of weight per unit area of 40gsm. The hydrophilic polyurethane film was also cut into pieces 8cm×12cm.

Pieces of spun-bonded polypropylene 7cm×10cm were placed on the non-adhesive side of the Kraton film and the hydrophilic polyurethane film placed on top of this. The Kraton and polyurethane films were then sealed together around their edges and around the polypropylene non-woven fabric using an impulse heat sealer to give the surgical dressing of the present invention.

The dressing may be sealed into a bacteria proof pack and sterilised using ethylene oxide.

Example 8

Preparation of Adhesive Surgical Dressing

An adhesive coated Kraton film was prepared using the method described in Example 7 to give an adhesive coated first layer which was 40cm wide. During the process of transfer coating of the adhesive onto the Kraton film two strips of polyester film, each approximately 4cm wide were adhered to each edge of the adhesive coated Kraton film to provide opposed non-adherent handles. The central 30cm portion of the adhesive coated film, that is the portion between the handles, was then perforated using an array of knife points to form a multiplicity of slits arranged in rows 1cm apart. The perforated laminate was then cut across its width to give pieces 40cm×30cm.

A piece of non-woven polypropylene material, approximately 27cm×27cm was then placed on the non-adherent perforated surface of the Kraton film so as to leave an eve margin around the non-woven material.

A continuous film, 30cm×30cm, of a hydrophilic polyurethane was formed by casting a solution of the polymer using the method described in Example 7. This film was placed over the non-woven material and then heat sealed around its edges to the Kraton film. The dressing so formed had non-adhesive handles on two opposite sides which may be used for manipulating the dressing during application and a central area of approximate area 30cm×30cm in which the adhesive coated first layer is perforated.

The dressings may be packaged into bacteria proof packs, sealed and sterilised using ethylene oxide.

The dressings of this particular size are useful in the treatment of skin graft donor sites.

Demonstration of Effectiveness

Moisture Vapour Permeability of Surgical Dressing Determination

A surgical dressing of the invention is applied adhesive face down, to an aluminium hot plate maintained at 35° C. The dressing covers a 2mm deep, 7.5cm in diameter recess in the plate. The recess is filled by a disc of polyurethane foam pre-soaked in horse serum. A hole in the bottom of the recess allows serum to be injected into the foam beneath the dressing. 3ml of serum are injected beneath the dressing to form a blister. The serum penetrates through the holes in the first layer so as to wet the surface of the continuous film and evaporate therefrom.

The moisture vapour transmission rate from the top of the dressing is measured using a Servo-Med Evaporimeter EPI (available from Servo-Med AB of Stockholm, Sweden) placed adjacent to the top of the dressing. The rate is measured when the 3ml of serum is injected and at specific intervals thereafter to follow changes in the rate as the volume of excess liquid diminishes.

A dressing of the invention formed according to the method described in Example 7 was tested in this manner. The dressing when placed on the metal plate was observed to adhere to the metal surface but did not adhere to the wet foam surface. The serum was observed to very rapidly penetrate the slits and to contact the underside of the upper, hydrophilic layer.

On removal of the dressing 48 hours after the injection of the serum it was observed that the surface of the foam was still moist but at no stage was a blister formed.

A comparative test with a conventional thin film moisture vapour permeable dressing showed a large blister of serum was still present beneath the dressing 48 hours after the injection of serum.

Measurements of the variation of moisture vapour transmission rate with time were performed using the Servo-Med Evaporimeter and gave the following results:

| Time after injection Stops (Hours) | Evaporimeter reading (g/m$^2$/hr) |
| --- | --- |
| 0 | 140 |
| 0.5 | 100 |
| 1.0 | 75 |
| 2.0 | 62 |
| 3.0 | 42 |
| 5.0 | 23 |
| 24.0 | 14 |
| 48.0 | 15 |

The results show a high moisture vapour transmission rate in the presence of serum which decreases to a low steady value as the volume of serum decreases. The top layer of the dressing at the end of the test was dry but the foam surface was still wet.

This illustrates the effectiveness of the dressings of the present invention in preventing blister formation whilst also preventing a drying out of the underlying surface.

A clinical trial was carried out on 9 patients involving 10 split skin graft donor sites. The dressings used were formed from a styrene-butadiene-styrene first layer coated with acrylic ester copolymer pressure sensitive adhesive and containing slits, an intermediate layer of non-woven polypropylene and a top layer of a hydrophilic polyurethane polymer which contained 25% by weight of water when hydrated. The size of the dressings was 40cm×30cm or 30cm×30cm and they were sterilised by ethylene oxide. The dressings were applied to the donor sites and left in position for 14 days. During this period it was observed that very little fluid collected under the dressings; water loss was high in the presence of fluid produced by the wound and lower in the absence of free fluid; the dressings were comfortable and easily removed and did not adhere to the wound. Seven of the 10 donor sites were observed to have healed within the 14 days of the test.

Test Methods

Measurement of Moisture Vapour Permeability

The moisture vapour permeability (MVP) of self-supporting materials, for example the continuous film and the first layer when unperforated (i.e. uninterrupted) may be measured by the Payne Cup method. This method uses a cup 1.5cm deep which has a flanged top. The inner diameter of the flange provides an area of 10cm$^2$ of material through which moisture vapour may pass. In this method 10ml of distilled water is added to the cup and a sample of the material under test, large enough to completely cover the flange, is clamped over the cup. When the test material has an adhesive surface it is clamped with the adhesive surface facing into the cup. The complete assembly is then weighed and placed in a fan assisted electric oven where the temperature and relative humidity are maintained at 37° C. and 10% respectively. The relative humidity within the oven is maintained at 10% by placing 1 Kg of anhydrous 3-8 mesh calcium chloride on the floor of the oven. After 24 hours the cup is removed from the oven and allowed to cool for 20 minutes to reach room temperature. After reweighing, the mass of water lost by vapour transmission is calculated. The moisture vapour permeability is expressed in units of $gm^{-2}24hr^{-1}$ at 37° C., 100% to 10% relative humidity difference, that is it is the mass of water transmitted through a square meter of material in a 24 hour period when maintained at 37° C. and there are differences of relative humidity at the two surfaces of the material of 100% inside the cup and 10% outside. The MVP is abbreviated to $g/m^2/24$ hr or $gm^{-2}24hr^{-1}$ when used herein. This is the moisture vapour permeability referred to herein unless otherwise stated. However, this permeability may also be referred to as the "upright-MVP" or "dry-MVP" to distinguish it from the "inverted-MVP" or "wet-MVP". The inverted-MVP is measured using the same apparatus as the upright-MVP except that when the cup is placed in the oven the cup is inverted so that liquid water (and not water vapour) is in contact with the test material and the test period is 24 hours.

The upright-MVP values of an adhesive film may be measured in the manner described above. The MVP of the adhesive layer can not usually be measured in this way because of the difficulty of preparing a self-supporting film of adhesive. However, the MVP of the adhesive may be obtained by coating a layer of adhesive onto a standard backing material of known thickness and MVP and using the relationship $P^{-1} = A^{-1} + B^{-1}$ in which P is the upright-MVP of the adhesive coated film, A is the upright-MVP of the adhesive layer and B is the upright-MVP of the standard backing layer. The backing material used as a standard is a continuous film of polyurethane having a thickness of 25 m, a weight per unit area of 30 gsm, a water content when fully hydrated of 2.5% by weight and an MVP of $1900g/m^2/24hr$. Thus since the value of P is measured and the value of B is known, the value of A may be calculated.

The MVP of the adhesive coated first layer may be measured on uninterrupted (unperforated) samples of the materials. However, if none are available a guide to the moisture vapour permeability of the adhesive coated first layer when unperforated (i.e. uninterrupted) may be determined from a sample of the perforated layer in the following way using the Payne Cup method. Two pieces of the adhesive-coated first layer of suitable size and possessing holes are taken and adhered together so that the holes in each sheet are offset from each other. In this way every hole is covered by an adhesive-coated layer of film that is the laminate is continuous. The moisture vapour permeability of the combined film is then measured using a Payne Cup. The desired MVP is taken as twice the measured value. If the holes form an appreciable area of the surface of the first layer then the multiplying factor is reduced in proportion to their area. For example an adhesive coated layer prepared using the process described in in Example 7 had a moisture vapour permeability when measured as an imperforate film of $237gm^{-2}24hr^{-1}$ whilst an offset double layer of the layer containing slits had a moisture vapour permeability of $121gm^{-1}$, thus leading to a calculated value of $242gm^{-2} 24hr^{-1}$ for a single layer which corresponds within experimental error to the actual measured value.

We claim:

1. An adhesive dressing suitable for use on moist wounds which dressing comprises a pressure sensitive adhesive-coated wound contacting first layer which has holes therethrough capable of transmitting liquid water and a moisture vapour permeable continuous film attached to the non-wound contacting surface of the first layer thereby forming a reservoir into which water can pass and evaporate therefrom, said adhesive coated first layer being of a material which has a moisture vapour permeability in the absence of holes therethrough of less than 300 $gm^{-2}$ and 24 $hr^{-1}$ and said moisture vapour permeable continuous film having a moisture vapour permeability which is greater when in contact with liquid water than when not in contact with liquid water.

2. An adhesive dressing suitable for use on moist wounds which dressing comprises a pressure sensitive adhesive-coated wound contacting first layer which has holes therethrough capable of transmitting liquid water and a moisture vapour permeable continuous film attached to the non-wound contacting surface of the first layer thereby forming a reservoir not which water can pass and a water transmitting intermediate layer present between the first layer and the continuous film, said adhesive coated first layer being of a material which has a moisture vapour permeability in the absence of holes therethrough of less than 300 $gm^{-2}$ and 24 $hr^{-1}$ and said moisture vapour permeable continuous film having a moisture vapour permeability which is greater when in contact with liquid water than when not in contact with liquid water.

3. A dressing according to claim 1 in which the adhesive coated first layer has a moisture vapour permeability in the absence of holes therethrough of from 20 to $280gm^{-2}24hr^{-1}$ when measured at 37° C. and 100% to 10% relative humidity.

4. A dressing according to claim 2 in which the adhesive coated first layer has a moisture vapour permeability in the absence of holes therethrough of from 20 to $280gm^{-2}24hr^{-1}$ when measured at 37° C. and 100% to 10% relative humidity.

5. A dressing according to claim 1 in which the continuous film has a moisture vapour permeability when not in contact with water of not more than $4800g\ m^{-2}\ 24hr^{-1}$ and a moisture vapour permeability when in contact with water of not less than $8000g\ m^{-2}\ 24hr^{-1}$.

6. A dressing according to claim 1 in which the continuous film is a hydrophilic polymer which when hydrated contains from 5 to 50% by weight water and is 15 and 80μm thick.

7. A dressing according to claim 6 in which the hydrophilic polymer is a hydrophilic polyurethane which when hydrated contains from 10 to 40% by weight of water.

8. A dressing according to claim 1 in which the first layer is a styrene-butadiene-styrene film and which is from 15 to 100μm thick.

9. A dressing according to either of claim 1 in which the pressure sensitive adhesive coated on the first layer comprises a polyvinyl ethyl ether adhesive or an acrylate ester copolymer adhesive which is present at a weight per unit area of from 20 to 80 gsm.

10. A dressing according to claim 2 in which the second water transmitting intermediate layer is a nonwoven fabric and is from 15 to 100μm thick.

11. A dressing according to claim 1 in which the holes in the adhesive coated first layer are in the form of slits which are from 0.3 to 1.4cm in length.

12. A dressing according to either of claim 1 in which the first layer extends beyond the edges of the continuous film on two opposed edges.

13. A dressing according to either of claim 1 in a sterile form packaged in a bacteria proof pack.

14. A method of dressing an exuding wound on an animal body which method comprises placing over the wound a dressing according to claim 1 and adhering the dressing to the body and leaving in position for a period of from 3 to 20 days.

15. A method of dressing a donor site on an animal body which comprises placing over the donor site a dressing according to claim 1 and adhering the dressing to the body and leaving in position for a period of from 3 to 20 days.

16. A method of dressing a donor site according to claim 14 in which the dressing is left in position for a period of 7 to 14 days.

* * * * *